United States Patent [19]

McLaughlin et al.

[11] Patent Number: 4,791,199

[45] Date of Patent: Dec. 13, 1988

[54] PROCESS FOR ANTIARRHYTHMIC 1,3-DIAZABICYCLO[4.4.0]DEC-2-EN-4-ONES

[75] Inventors: Kathleen T. McLaughlin, Arlington Heights; Robert J. Chorvat, Lake Bluff; Kathleen A. Prodan, Buffalo Grove, all of Ill.

[73] Assignee: G. D. Searle & Co., Chicago, Ill.

[21] Appl. No.: 777,661

[22] Filed: Sep. 19, 1985

[51] Int. Cl.$^4$ ............................................. C07D 471/04
[52] U.S. Cl. ..................................... 544/282; 546/226; 546/233
[58] Field of Search ................................ 544/282, 319

[56] References Cited

U.S. PATENT DOCUMENTS 4,560,754 12/1985 Adelstein et al. ................... 544/282
4,585,863 4/1986 Deinhammer et al. ............. 544/319
4,680,295 7/1987 Fowler et al. ....................... 514/258

FOREIGN PATENT DOCUMENTS 0104647 4/1984 European Pat. Off. .

*Primary Examiner*—Donald G. Daus
*Assistant Examiner*—E. Bernhardt
*Attorney, Agent, or Firm*—Frank P. Grassler; J. Timothy Keane; Paul D. Matukaitis

[57] ABSTRACT

This invention relates to a process for preparing useful antiarrhythmic 1,3-diazabicyclo[4.4.0]dec-2-en-4-ones from 1-acyl-α-[2-[bis(1-methylethyl)amino]ethyl]-α-phenyl-2-piperidineacetamides. This invention also relates to the 1-acyl-α-[2-[bis(1-methylethyl)amino]ethyl]-α-phenyl-2-piperidineacetamides employed in this process.

12 Claims, No Drawings

PROCESS FOR ANTIARRHYTHMIC 1,3-DIAZABICYCLO[4.4.0]DEC-2-EN-4-ONES

BACKGROUND OF THE INVENTION (a) Field of the Invention

This invention relates to a novel process that permits the unexpectedly efficient and convenient preparation of antiarrhythmic 1,3-diazabicyclo[4.4.0]dec-2-en-4-ones (hereinafter "diazabicyclodecenones") of Formula II of the copending U.S. patent application, Ser. No. 06/635,989, now U.S. Pat. No. 4,560,754, having the same assignee as the present application, using 1-acyl-α-[2-[bis(1-methylethyl)amino]ethyl]-α-phenyl-2-piperidineacetamides of Formula I.

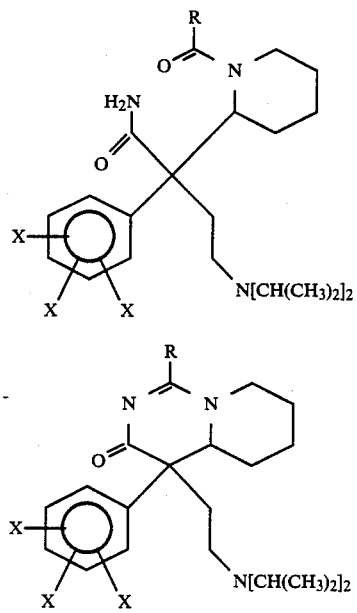

More specifically, this invention relates to a process for preparing diazabicyclodecenones of Formula II in improved overall yield and purity by acylating α-[2-[bis(1-methylethyl)amino]ethyl]-α-phenyl-2-piperidineacetamides and then treating the resultant 1-acyl-α-[2-[bis(1-methylethyl)amino]ethyl]-α-phenyl-2-piperidineacetamides of Formula I with a strong base in a polar organic solvent.

This invention also relates to the 1-acyl-α-[2-[bis(1-methylethyl)amino]ethyl]-α-phenyl-2-piperidineacetamides of Formula I employed in the preparation of the antiarrhythmic diazabicyclodecenones of Formula II.

(b) Prior Art

Antiarrhythmic 1,3-diazabicyclo[4.4.0]dec-2-en-4-ones of Formula II have been disclosed in European patent publication No. 104,647, filed Sept. 27, 1983, and in copending U.S. patent application, Ser. No. 06/635,989, now U.S. Pat. No. 4,560,754, both having the same assignee as the present application. The process of this invention and the 1-acyl-α-[2-[bis(1-methylethyl)amino]ethyl]-α-phenyl-2-piperidineacetamides, Formula I, of this invention were disclosed but not claimed in copending Ser. No. 635,989.

SUMMARY OF THE INVENTION

This invention relates to a process for preparing 1,3-diazabicyclo[4.4.0]dec-2-en-4-ones, Formula II, of copending Ser. No. 06/635,989, now U.S. Pat. No. 4,560,754, by treating 1-acyl-2-piperidineacetamides of Formula I with a strong base in a polar organic solvent. The diazabicyclodecenones thus formed are isolated and purified, generally by solvent-solvent extraction and recrystallization. The process permits the preparation of compounds of Formula II with improved overall yield and purity when compared with the method described in U.S. Pat. No. 4,560,754 using a dialkyl ketal or acetal of an amide, an orthoester, or other acyl equivalents to induce cyclization.

This invention also relates to compounds of Formula I:

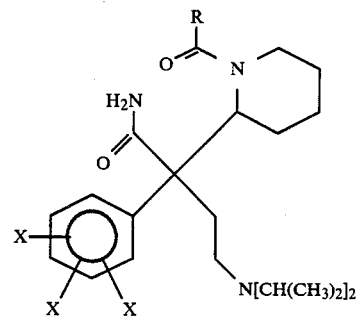

or isomers or racemates thereof; wherein R is
(a) hydrogen
(b) alkyl of 1 to 6 carbon atoms, inclusive; or
(c)

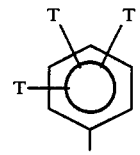

wherein each T is a substituent taken independently, selected from the group consisting of:
(a) hydrogen
(b) halogen;
(c) alkyl of 1 to 6 carbon atoms, inclusive;
(d) alkoxy of 1 to 6 carbon atoms, inclusive; or
(e) phenyl;
wherein each X is a substituent taken independently, selected from the group consisting of:
(a) hydrogen;
(b) halogen;
(c) alkyl of 1 to 6 carbon atoms, inclusive;
(d) alkoxy of 1 to 6 carbon atoms, inclusive; or
(e) phenyl.

Examples of alkyl of 1 to 6 carbon atoms, inclusive, are methyl, ethyl, propyl, butyl, pentyl, hexyl, and the isomeric forms thereof, generally referred to as lower alkyl.

Examples of alkoxy of 1 to 6 carbon atoms, inclusive, are methoxy, ethoxy, propoxy, butoxy, pentoxy, hexoxy, and the isomeric forms thereof.

Examples of halogen are fluorine, chlorine, bromine, and iodine.

DESCRIPTION OF THE INVENTION

The compounds of this invention are prepared by the following general method from α-[2-[bis(1-methylethyl)amino]ethyl]-α-phenyl-2-piperidineacetamides of Formula III, which are prepared as described in copending U.S. patent application, Ser. No. 06/635,989, now U.S. Pat. No. 4,560,754.

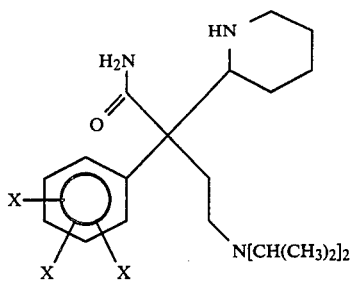

Compounds of Formula III are initially acylated by methods known to those in the art to form the compounds of this invention, Formula I. Where R is alkyl or optionally substituted phenyl, as defined above, preferred acylating conditions include reaction of a compound of Formula III with a carboxylic acid anhydride of the formula (R—CO)$_2$O at room temperature, with or without solvent. If the carboxylic acid anhydride is a solid, preferred conditions include using a relatively unreactive organic solvent, such as dimethylformamide; however, if the carboxylic acid anhydride is a liquid, preferred conditions employ no separate solvent. Where R is hydrogen, preferred acylating conditions include reaction of a compound of Formula III with a mixed anhydride of formic acid, such as acetic formic anhydride.

Compounds of Formula II are prepared by the following general method from compounds of Formula I. The compounds of Formula I are dissolved in a polar organic solvent to which is added a strong base. Suitable polar organic solvents include dimethylsulfoxide; N,N-disubstituted amides, such as dimethylformamide, dimethylacetamide, 1-methyl-2-pyrrolidinone, and the like; ketones, such as acetone, methyl ethyl ketone, and the like; and alcohols, such as methanol, ethanol, propanol, isopropyl alcohol, and the like. Preferred polar organic solvents include dimethylsulfoxide and acetone. For purposes of this application the term "strong base" refers to a substance sufficiently basic to induce cyclization by abstracting a proton from the amide NH$_2$ group. Suitable strong bases include alkali metal hydroxides, such as sodium hydroxide, potassium hydroxide, and the like, preferably in powdered form; alkali metal alkoxides, such as sodium methoxide, sodium ethoxide, potassium t-butoxide, and the like; alkaline earth hydroxides, such as calcium hydroxide, barium hydroxide, and the like, preferably in powdered form; quaternary ammonium hydroxides, such as tetramethylammonium hydroxide and the like; and other strong bases known in the art. Preferred strong bases include powdered sodium hydroxide and powdered potassium hydroxide. Although considerably less than molar equivalent quantities of strong base are sufficient to effect the cyclization, preferred conditions include approximately one molar quantity of sodium or potassium hydroxide for each molar quantity of a compound of Formula I.

Isolation of the resultant compounds of Formula II involves solvent-solvent extraction using water and a water-immiscible organic solvent. Water-immiscible organic solvents include aliphatic hydrocarbons, such as hexane, heptane, and the like; halogenated hydrocarbons, such as chloroform, dichloromethane, and the like; esters, such as ethyl acetate and the like; aromatic hydrocarbons, such as toluene and the like; and other such organic solvents. Preferred water-immiscible organic solvents include dichloromethane and ethyl acetate. Where the reaction solvent is high-boiling, a mixture of water and the organic solvent may be added directly to the reaction mixture before performing the extractions. Where the reaction solvent is low-boiling, the reaction solvent may be removed by concentration in vacuo before adding the water and water-immiscible organic solvent and performing the extractions. In either case, the aqueous and organic solvent components separate into layers. In one variation of the extraction, the organic layer containing compounds of Formula II is separated from the aqueous layer (with appropriate back-washing as customary in the art), dried over a drying agent (such as sodium sulfate and the like) and concentrated in vacuo. In another variation of the extraction, the layered aqueous and organic components are acidified with any suitable mineral acid (such as hydrochloric or sulfuric acid) before the layers are physically separated. In this variation, the acidic aqueous layer containing the compounds of Formula II (in acid addition salt form) is separated from the organic layer. The aqueous layer is then made basic with any suitable inorganic base (such as sodium carbonate, sodium hydroxide, and the like) and again extracted with a water-immiscible organic solvent. The organic layer is then separated, dried, and concentrated in the same manner as used in the first extraction variation. After using either extraction variation, the compounds of Formula II may be purified from the resultant residue by means known in the art, such as by recrystallization from a suitable solvent or solvent mixture, such as toluene-heptane; by chromatography, preferably using silica gel; or by simple trituration with an organic solvent in which the desired compounds are relatively insoluble, as may be readily determined by one skilled in the art.

The preferred embodiments of this invention include compounds of the following general structure, Formula IV, used in the preparation of corresponding antiarrhythmic diazabicyclodecenones.

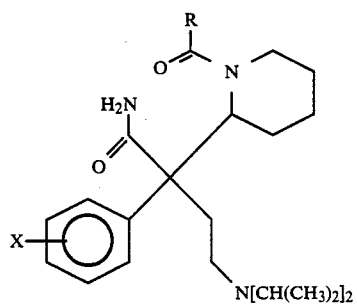

More specifically, the preferred embodiments include compounds of Formula IV wherein R is alkyl of 1 to 6 carbon atoms, inclusive, or phenyl; and wherein X is hydrogen, halogen, alkyl of 1 to 6 carbon atoms, inclusive, alkoxy of 1 to 6 carbon atoms, inclusive, or phenyl.

The most preferred embodiments of this invention includes compounds of the following general structure, Formula V, used in the preparation of corresponding antiarrhythmic diazabicyclodecenones.

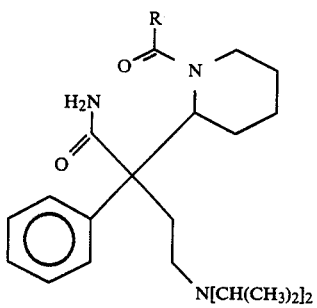

More specifically, the most preferred embodiments include compounds of Formula V wherein R is alkyl of 1 to 6 carbon atoms, inclusive, or phenyl.

The following examples further illustrate details for the preparation of the compounds of this invention and subsequent conversion to diazabicyclodecenones, Formula II, of copending Ser. No. 06/635,989, now U.S. Pat. No. 4,560,754. The invention, which is set forth in the foregoing disclosure, is not to be construed or limited in spirit or in scope by these examples. Those skilled in the art will readily understand that known variations of the conditions of the following preparative procedures can be used to prepare these compounds. All temperatures are degrees celsius unless otherwise noted.

DESCRIPTION OF THE PREFERRED EMBODIMENTS

Example 1

α-[2-[bis(1-methylethyl)amino]ethyl]-α-phenyl-2-piperidineacetamide, Racemate A

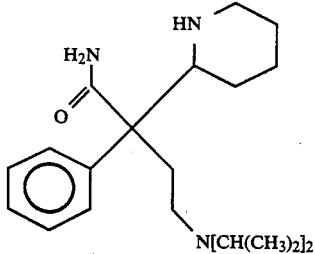

A mixture of 105.3 g (0.31 mole) of racemic 2-phenyl-2-(2-pyridyl)-4-[N,N-bis(1-methylethyl)amino]butanamide and 27 ml (ca. 0.32 mole) of concentrated aqueous hydrochloric acid in 2.5 liters of ethanol was hydrogenated at 50 psi over platinum oxide catalyst. After filtration to remove the catalyst, the reaction mixture was reduced to a syrupy residue, dissolved in an ice-water mixture, and neutralized with a slight excess of 25% sodium hydroxide. The product was extracted into diethyl ether, which was then dried over magnesium sulfate, filtered, and concentrated to dryness. The crude product was crystallized twice from Skellysolve B containing a small amount of diethyl ether, affording 26.0 g of the title compound as a white solid, m.p. 107°–108°. Structure assignment was confirmed by proton and carbon-13 nmr spectra and by elemental analysis.

Proton nmr (CDCl$_3$): δ (ppm) 0.83, 0.92, 7.33.

Example 2

α-[2-[bis(1-methylethyl)amino]ethyl]-α-phenyl-2-piperidineacetamide, Racemate B

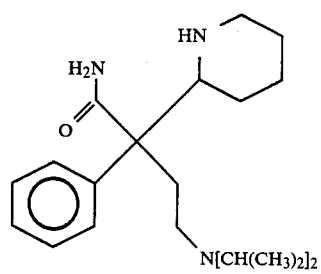

The final filtrate from Example 1 was concentrated under a stream of nitrogen to an oil that slowly solidified. The crude material was chromatographed several times on silica gel to yield a total of 17 g of the title compound as a white solid, m.p. 81°–82°. Structure assignment was confirmed by proton and carbon-13 nmr spectra and by elemental analysis.

Proton nmr (CDCl$_3$): δ (ppm) 0.96, 1.05, 7.30.

Example 3

1-acetyl-α-[2-[bis(1-methylethyl)amino]ethyl]-α-phenyl-2-piperidineacetamide, Racemate A (Procedure A)

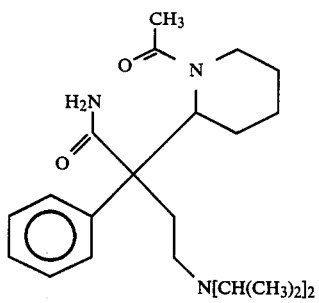

A mixture of 4.2 kg (12 moles) of the title product of Example 1 and 9.7 liters (103 moles) of acetic anhydride was stirred under dry nitrogen at room temperature for twenty-three hours. After diluting with 13 liters of dichloromethane, the reaction mixture was added with stirring to 75 liters of 3M ammonium hydroxide cooled to 10°. After one hour the mixture was allowed to separate into layers. The organic layer was separated and the aqueous layer extracted with dichloromethane. The combined organic layers were then washed with water, dried over sodium sulfate, filtered, and concentrated in vacuo to dryness, giving the N-acetylated title compound. Structure assignment was confirmed by the proton nmr spectrum and by elemental analysis.

Proton nmr (CDCl$_3$): δ (ppm) 0.93, 1.05, 2.10, 7.4.

Example 4

1-acetyl-α-[2-[bis(1-methylethyl)amino]ethyl]-α-phenyl-2-piperidineacetamide, Racemate A (Procedure B)

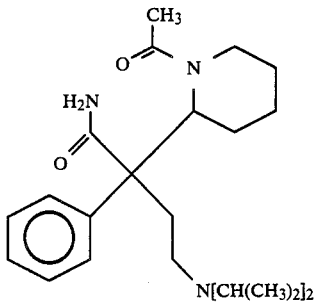

The title compound was prepared by the method of Example 3 from 52.1 kg of the title product of Example 1 and 130 kg (1273 moles) of acetic anhydride. Potassium carbonate (253 kg, 1830 moles) in 760 liters of water was used instead of aqueous ammonium hydroxide to quench the reaction. Extractions were performed as in Example 3. The title compound was used in subsequent reactions without further purification.

Example 5

1-acetyl-α-[2-[bis(1-methylethyl)amino]ethyl]-α-phenyl-2-piperidineacetamide, Racemate B

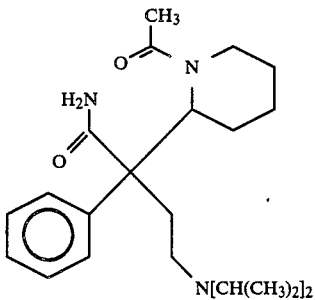

The title compound (3.6 g) was prepared by the method of Example 3 using the title compound of Example 2 instead of the title product of Example 1. Extractions were performed with ethyl acetate instead of dichloromethane. Structure assignment was confirmed by the proton nmr spectrum.

Proton nmr (CDCl₃): δ (ppm) 0.90, 0.94, 0.98, 1.03, 2.15, 7.3.

Example 6

2-methyl-5-phenyl-5-[2-[N,N-bis(1-methylethyl)amino]ethyl]-1,3-diazabicyclo[4.4.0]dec-2-en-4-one, Racemate A (Procedure C)

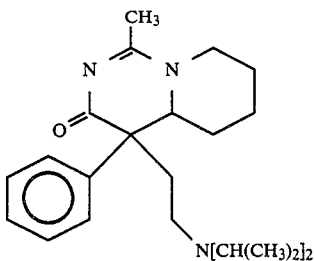

A mixture of the title product of Example 3 and 0.8 kg (12 moles) of powdered potassium hydroxide in 15 liters of dimethylsulfoxide was stirred under dry nitrogen at room temperature for two hours. Approximately 20 liters of dichloromethane and 85 liters of water were added, and the mixture was stirred for thirty minutes. The organic layer was separated and the aqueous layer was extracted with dichloromethane. The combined organic layers were washed with water, dried over sodium sulfate, filtered, and concentrated in vacuo to dryness. The residue was dissolved in 15 liters of refluxing toluene. After cooling below 60°, the solution was diluted with 15 liters of heptane and cooled to 10°. The title compound, m.p. 195.5°–197°, was collected in two crops.

Example 7

2-methyl-5-phenyl-5-[2-[N,N-bis(1-methylethyl)amino]ethyl]-1,3-diazabicyclo[4.4.0]dec-2-en-4-one, Racemate A (Procedure D)

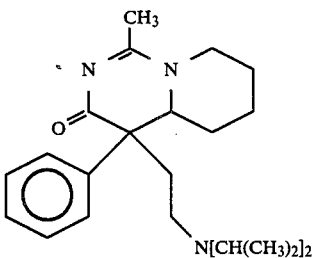

A mixture of the title product of Example 4 and 9.4 kg (151 moles) of powdered potassium hydroxide (90% pure) in 400 liters of acetone was stirred under dry nitrogen at room temperature for two hours. The mixture was concentrated in vacuo to dryness and the residue was dissolved in approximately 250 liters of dichloromethane and 250 liters of water. After the mixture was cooled to less than 20°, 18M sulfuric acid (13.8 liters, 248 moles) was added. The organic layer was separated and extracted with several portions of water. The aqueous layers were combined and washed with dichloromethane. The acidic aqueous layer was then diluted with 250 liters of dichloromethane. After the mixture was cooled to less than 20°, 50% aqueous sodium hydroxide (30.56 kg, 382 moles) was added. The basic aqueous layer was separated and extracted with several portion of dichloromethane. The organic layers were combined and then washed with brine, dried over sodium sulfate, filtered, and concentrated in vacuo to dryness. The residue was dissolved in 160 liters of refluxing toluene. After cooling below 80°, the solution was diluted with 160 liters of heptane and cooled to 10°. The title compound, m.p. 200°-204°, was collected in two crops. Spectral and elemental data were consistent with the assigned structure.

Proton nmr (CDCl₃): δ (ppm) 0.80, 1.95, 7.25.

Analysis. Calcd. for $C_{23}H_{35}N_3O$: C, 74.75; H, 9.55; N, 11.37. Found: C, 75.02, 74.90; H, 9.47, 9.46; N, 11.38, 11.37.

Example 8

2-methyl-5-phenyl-5-[2-[N,N-bis(1-methylethyl)amino]ethyl]-1,3-diazabicyclo[4.4.0]dec-2-en-4-one, Racemate B (Procedure C)

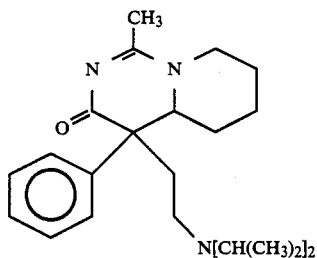

The title compound, m.p. 177°-178°, was prepared by the general method of Example 6 using the title product of Example 5 instead of the title product of Example 3. Structure assignment was confirmed by the proton nmr spectrum.

Proton nmr (CDCl₃): δ (ppm) 0.85-0.95, 2.20, 7.2-7.65.

Analysis. Calcd. for $C_{23}H_{35}N_3O$: C, 74.75; H, 9.55; N, 11.37. Found: C, 74.84; H, 9.61; N, 11.26.

Example 9

2-methyl-5-phenyl-5-[2-[N,N-bis(1-methylethyl)amino]ethyl]-1,3-diazabicyclo[4.4.0]dec-2-en-4-one, Racemate B (Procedure D)

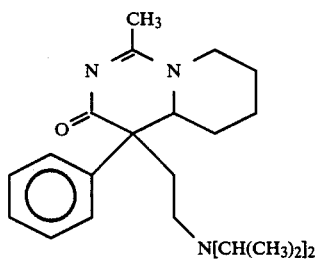

The title compound is prepared by the general method of Example 7 using the title product of Example 5 instead of the title product of Example 3.

Example 10

α-[2-[bis(1-methylethyl)amino]ethyl]-1-(1-oxopropyl)-α-phenyl-2-piperidineacetamide, Racemate A

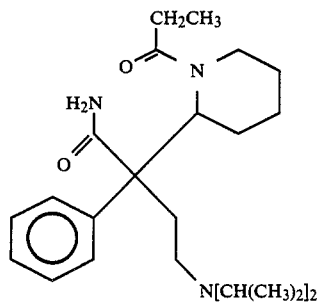

The title compound was prepared by the general method of Example 3 using propanoic anhydride instead of acetic anhydride. Extractions were performed using ethyl acetate instead of dichloromethane and brine instead of water. Chromatography on silica gel afforded 14.2 g of the title compound as an oil. Structure assignment was confirmed by the proton nmr spectrum.

Proton nmr (CDCl₃): δ (ppm) 0.90, 1.00, 2.25 (t), 7.3.

Example 11

2-ethyl-5-phenyl-5-[2-[N,N-bis(1-methylethyl)amino]ethyl]-1,3-diazabicyclo[4.4.0]dec-2-en-4-one, Racemate A

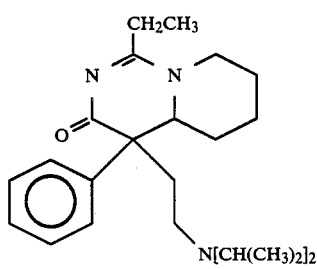

The title compound, m.p. 145°-147°, was prepared by the general method of Example 6 using the title product of Example 10 instead of the title product of Example 3. Structure assignment was confirmed by the proton nmr spectrum.

Proton nmr (CDCl₃): δ (ppm) 0.90, 7.25.

Analysis. Calcd. for $C_{24}H_{37}N_3O$: C, 75.15; H, 9.72; N, 10.95. Found: C, 74.89; H, 9.68; N, 10.79.

Example 12

1-benzoyl-α-[2-[bis(1-methylethyl)amino]ethyl]-α-phenyl-2-piperidineacetamide, Racemate A

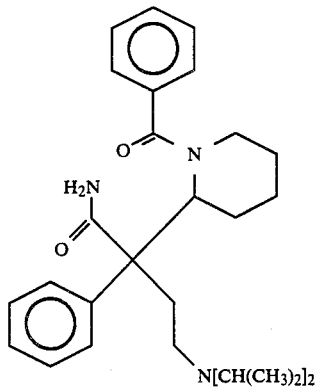

The title compound was prepared by the general method of Example 3 using benzoic anhydride in dimethylformamide instead of acetic anhydride. Extractions were performed with diethyl ether instead of dichloromethane. Trituration of the resultant gum with chloroform produced a white solid. Structure assignment was confirmed by infrared and proton nmr spectra and by elemental analysis.

Proton nmr (CDCl$_3$): δ (ppm) 0.93, 1.00, 7.3, 7.5.

Analysis. Calcd. for C$_{28}$H$_{39}$N$_3$O$_2$: C, 74.80; H, 8.74; N, 9.35. Found: C, 75.74; H, 8.79; N, 9.30.

Example 13

2,5-diphenyl-5-[2-[N,N-bis(1-methylethyl)amino]ethyl]-1,3-diazabicyclo[4.4.0]dec-2-en-4-one, Racemate A

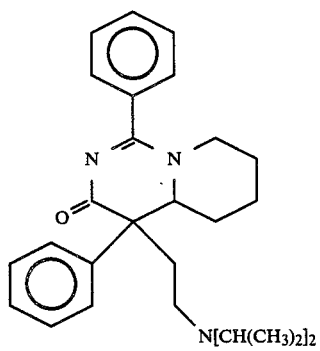

To a mixture of 20.6 g of the title product of Example 12 in 130 ml of dimethylformamide was added 8.0 g powdered potassium hydroxide. After the reaction mixture was stirred overnight, 250 ml of water was added in portions with vigorous stirring. Crude title compound was collected by filtration and dried, then triturated with 75 ml of boiling ethyl acetate. After cooling, the title compound was collected as white needles, m.p. 221°–222°. Structure assignment was confirmed by the proton nmr spectrum and by elemental analysis.

Proton nmr (CDCl$_3$): δ (ppm) 0.85, 7.12–7.35

Analysis. Calcd. for C$_{28}$H$_{37}$N$_3$O: C, 77.92; H, 8.64; N, 9.74. Found: C, 77.95; H, 8.66; N, 9.86.

What is claimed is:

1. A process for preparing a 1,3-diazabicyclo[4.4.0]-dec-2-en-4-one of the formula

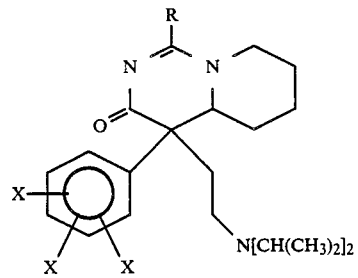

or an isomer of a racemate thereof, wherein R is:
(a) hydrogen
(b) alkyl of 1 to 6 carbon atoms, inclusive; or
(c)

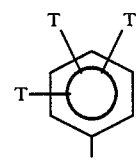

wherein each T is a substituent taken independently, selected from the group consisting of:
(a) hydrogen
(b) halogen;
(c) alkyl of 1 to 6 carbon atoms, inclusive;
(d) alkoxy of 1 to 6 carbon atoms, inclusive; or
(e) phenyl;

wherein each X is a substituent taken independently, selected from the group consisting of:
(a) hydrogen;
(b) halogen;
(c) alkyl of 1 to 6 carbon atoms, inclusive;
(d) alkoxy of 1 to 6 carbon atoms, inclusive; or
(e) phenyl comprising
(a) acylating a 2-piperidineacetamide of the formula

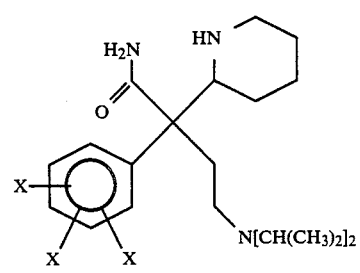

or an isomer or a racemate thereof, wherein T and X are defined as above, to form a 1-acyl-2-piperidineacetamide of the formula

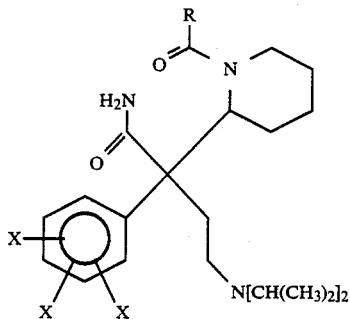

or an isomer or a racemate thereof, wherein R, T, and X are defined as above; and (b) cyclizing the 1-acyl-2-piperidineacetamide with a strong base taken from the group consisting of alkali metal hydroxides, alkali metal alkoxides, alkaline earth hydroxides, and quaternary ammonium hydroxides in a polar organic solvent.

2. A process according to claim 1 wherein the strong base is an alkali metal hydroxide.

3. A process according to claim 2 wherein the polar organic solvent is dimethylsulfoxide or acetone.

4. A process according to claim 3 comprising
(a) acylating a 2-piperidineacetamide with a carboxylic acid anhydride to form a 1-acyl-2-piperidineacetamide; and
(b) cyclizing the 1-acyl-2-piperidineacetamide with an alkali metal hydroxide in dimethylsulfoxide.

5. A process according to claim 4 comprising
(a) acylating a 2-piperidineacetamide with a carboxylic acid anhydride to form a 1-acyl-2-piperidineacetamide;
(b) cyclizing the 1-acyl-2-piperidineacetamide with postassium hydroxide in dimethylsulfoxide; and
(c) isolating the 1,3-diazabicyclo[4.4.0]dec-2-en-4-one by solvent-solvent extraction, using water and a water-immiscible organic solvent taken from the group consisting of aliphatic hydrocarbons, halogenated hydrocarbons, alkyl esters and aromatic hydrocarbons.

6. A process according to claim 5 comprising
(a) acylating α-[2-[bis(1-methylethyl)amino]ethyl]-α-phenyl-2-piperidineacetamide with acetic anhydride to form 1-acetyl-α-[2-[bis(1-methylethyl)amino]ethyl]-α-phenyl-2-piperidineacetamide;
(b) cyclizing 1-acetyl-α-[2-[bis(1-methylethyl)amino]ethyl]-α-phenyl-2-piperidineacetamide with potassium hydroxide in dimethylsulfoxide; and
(c) isolating 2-methyl-5-phenyl-5-[2-[N,N-bis(1-methylethyl)amino]ethyl]-1,3-diazabicyclo[4.4.0]-dec-2-en-4-one by solvent-solvent extraction.

7. A process according to claim 5 comprising
(a) acylating α-[2-[bis(1-methylethyl)amino]ethyl]-α-phenyl-2-piperidineacetamide with propanoic anhydride to form α-[2-[bis(1-methylethyl)amino]ethyl]-1-(1-oxopropyl)-α-phenyl-2-piperidineacetamide;
(b) cyclizing α-[2-[bis(1-methylethyl)ethyl]-1-(1-oxopropyl)-α-phenyl-2-piperidineacetamide with potassium hydroxide in dimethylsulfoxide; and
(c) isolating 2-ethyl-5-phenyl-5-[2-[N,N-bis(1-methylethyl)amino]ethyl]-1,3-diazabicyclo[4.4.0]-dec-2-en-4-one by solvent-solvent extraction.

8. A process according to claim 5 comprising
(a) acylating α-[2-[bis(1-methylethyl)amino]ethyl]-α-phenyl-2-piperidineacetamide with benzoic anhydride to form 1-benzoyl-α-[2-[bis(1-methylethyl)amino]ethyl]-α-phenyl-2-piperidineacetamide;
(b) cyclizing 1-benzoyl-α-[2-[bis(1-methylethyl)amino]ethyl]-α-phenyl-2-piperidineacetamide with potassium hydroxide in dimethylsulfoxide; and
(c) isolating 2,5-diphenyl-5-[2-[N,N-bis(1-methylethyl)amino]ethyl]-1,3-diazabicyclo[4.4.0]dec-2-en-4-one by solvent-solvent extraction.

9. A process according to claim 4 comprising
(a) acylating a 2-piperidineacetamide with a carboxylic acid anhydride to form a 1-acyl-2-piperidineacetamide;
(b) cyclizing the 1-acyl-2-piperidineacetamide with potassium hydroxide in acetone; and
(c) isolating the 1,3-diazabicyclo[4.4.0]dec-2-en-4-one by solvent-solvent extraction.

10. A process according to claim 9 comprising
(a) acylating α-[2-[bis(1-methylethyl)amino]ethyl]-α-phenyl-2-piperidineacetamide with acetic anhydride to form 1-acetyl-α-[2-[bis(1-methylethyl)amino]ethyl]-α-phenyl-2-piperidineacetamide;
(b) cyclizing 1-acetyl-α-[2-[bis(1-methylethyl)amino]ethyl]-α-phenyl-2-piperidineacetamide with potassium hydroxide in acetone; and
(c) isolating 2-methyl-5-phenyl-5-[2-[N,N-bis(1-methylethyl)amino]ethyl]-1,3-diazabicyclo[4.4.0]-dec-2-en-4-one by solvent-solvent extraction.

11. A process according to claim 9 comprising
(a) acylating α-[2-[bis(1-methylethyl)amino]ethyl]-α-phenyl-2-piperidineacetamide with propanoic anhydride to form α-[2-[bis(1-methylethyl)amino]ethyl]-1-(1-oxopropyl)-α-phenyl-2-piperidineacetamide;
(b) cyclizing α-[2-[bis(1-methylethyl)amino]ethyl]-1-(1-oxopropyl)-α-phenyl-2-piperidineacetamide with potassium hydroxide in acetone; and
(c) isolating 2-ethyl-5-phenyl-5-[2-[N,N-bis(1-methylethyl)amino]ethyl]-1,3-diazabicyclo[4.4.0]-dec-2-en-4-one by solvent-solvent extraction.

12. A process according to claim 9 comprising
(a) acylating α-[2-[bis(1-methylethyl)amino]ethyl]-α-phenyl-2-piperidineacetamide with benzoic anhydride to form 1-benzoyl-α-[2-[bis(1-methylethyl)amino]ethyl]-α-phenyl-2-piperidineacetamide;
(b) cyclizing 1-benzoyl-α-[2-[bis(1-methylethyl)amino]ethyl]-α-phenyl-2-piperidineacetamide with potassium hydroxide in acetone; and
(c) isolating 2,5-diphenyl-5-[2-[N,N-bis(1-methylethyl)amino]ethyl]-1,3-diazabicyclo[4.4.0]dec-2-en-4-one by solvent-solvent extraction.

* * * * *